(12) United States Patent
Imamura et al.

(10) Patent No.: US 9,031,301 B2
(45) Date of Patent: May 12, 2015

(54) IMAGE PROCESSING APPARATUS AND MEDICAL IMAGE DIAGNOSIS APPARATUS

(71) Applicants: Kabushiki Kaisha Toshiba, Tokyo (JP); Toshiba Medical Systems Corporation, Otawara-Shi (JP)

(72) Inventors: Tomohisa Imamura, Nasushiobara (JP); Kuramitsu Nishihara, Otawara (JP); Takuya Sasaki, Nasu-gun (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 36 days.

(21) Appl. No.: 14/074,804

(22) Filed: Nov. 8, 2013

(65) Prior Publication Data

US 2014/0064590 A1    Mar. 6, 2014

Related U.S. Application Data

(63) Continuation of application No. PCT/JP2012/074081, filed on Sep. 20, 2012.

(30) Foreign Application Priority Data

Sep. 20, 2011 (JP) ................................. 2011-205130
Sep. 20, 2012 (JP) ................................. 2012-207033

(51) Int. Cl.
*G06K 9/00* (2006.01)
*G06T 11/00* (2006.01)
(Continued)

(52) U.S. Cl.
CPC ............... *G06T 11/003* (2013.01); *A61B 6/00* (2013.01); *A61B 6/03* (2013.01); *A61B 8/00* (2013.01);
(Continued)

(58) Field of Classification Search
USPC ................................................ 382/131, 298
See application file for complete search history.

(56) References Cited

U.S. PATENT DOCUMENTS 7,532,771 B2     5/2009 Taylor et al.
2007/0223887 A1*  9/2007 Kanamori et al. ............ 386/112
(Continued)

FOREIGN PATENT DOCUMENTS

CN     101197043 A       6/2008
CN     101197043 B   *   6/2008   ................ G06T 3/40
(Continued)

OTHER PUBLICATIONS

Combined Chinese Office Action and Search Report issued Jul. 11, 2014 in Patent Application No. 201280002656.6 (with English translation of categories of cited documents).
(Continued)

*Primary Examiner* — Gregory F Cunningham
(74) *Attorney, Agent, or Firm* — Oblon, McClelland, Maier & Neustadt, L.L.P.

(57) ABSTRACT

An image processing apparatus includes: an enlarging unit that enlarges target data by using an enlargement factor based on an optimal sample number indicating a quantity of samples per unit length suitable for an image processing process; a decomposing unit that generates a group of data satisfying the optimal sample number by performing a decomposing process realized by a multi-resolution analysis on the enlarged data; a data processing unit that generates an already-processed group of data by performing the image processing process on the group of data satisfying the optimal sample number; a reconstructing unit that generates reconstructed data by performing a reconstructing process realized by a multi-resolution analysis on the already-processed group of data; and a reducing unit that reduces the reconstructed data in such a manner that the quantity of samples per unit length becomes equal to the quantity of samples per unit length in the target data.

8 Claims, 13 Drawing Sheets

(51) Int. Cl.
  *A61B 6/00* (2006.01)
  *A61B 6/03* (2006.01)
  *A61B 8/00* (2006.01)
  *G06T 1/00* (2006.01)
  *A61B 8/08* (2006.01)
  *G06T 3/40* (2006.01)
  *A61B 5/055* (2006.01)

(52) U.S. Cl.
  CPC . *A61B 5/055* (2013.01); *G06T 1/00* (2013.01); *A61B 6/5205* (2013.01); *A61B 8/461* (2013.01); *A61B 8/469* (2013.01); *A61B 8/488* (2013.01); *A61B 8/5207* (2013.01); *G06T 3/40* (2013.01)

(56) References Cited

U.S. PATENT DOCUMENTS

| | | | |
|---|---|---|---|
| 2009/0088638 | A1 | 4/2009 | Sato et al. |
| 2010/0228129 | A1 | 9/2010 | Osumi |
| 2010/0286525 | A1 | 11/2010 | Osumi |
| 2012/0035478 | A1 | 2/2012 | Nishihara et al. |

FOREIGN PATENT DOCUMENTS

| | | | |
|---|---|---|---|
| JP | 2006-041744 | 2/2006 | |
| JP | 2008-204441 | 9/2008 | |
| JP | 2009-082469 | 4/2009 | |
| JP | 2010-512607 | 4/2010 | |
| JP | 2010-227554 | 10/2010 | |
| JP | 2010-259658 | 11/2010 | |
| WO | WO 2006079991 A2 * | 8/2006 | ............... G06K 9/36 |

OTHER PUBLICATIONS

Richard Szeliski, "Computer vision: Algorithms and applications", Springer, Sep. 3, 2010, pp. 144-265 and Cover Page.
International Search Report mailed Oct. 16, 2012 in PCT/JP2012/074081, filed Sep. 20, 2012 (with English Translation).
Written Opinion of the International Searching Authority mailed Oct. 16, 2012 in PCT/JP2012/074081, filed Sep. 20, 2012.

* cited by examiner

FIG.2

| IMAGE PROCESSING | OPTIMAL SAMPLE NUMBER |
|---|---|
| A | a |
| B | b |
| C | c |
| ⋮ | ⋮ |
| ⋮ | ⋮ |
| ⋮ | ⋮ |

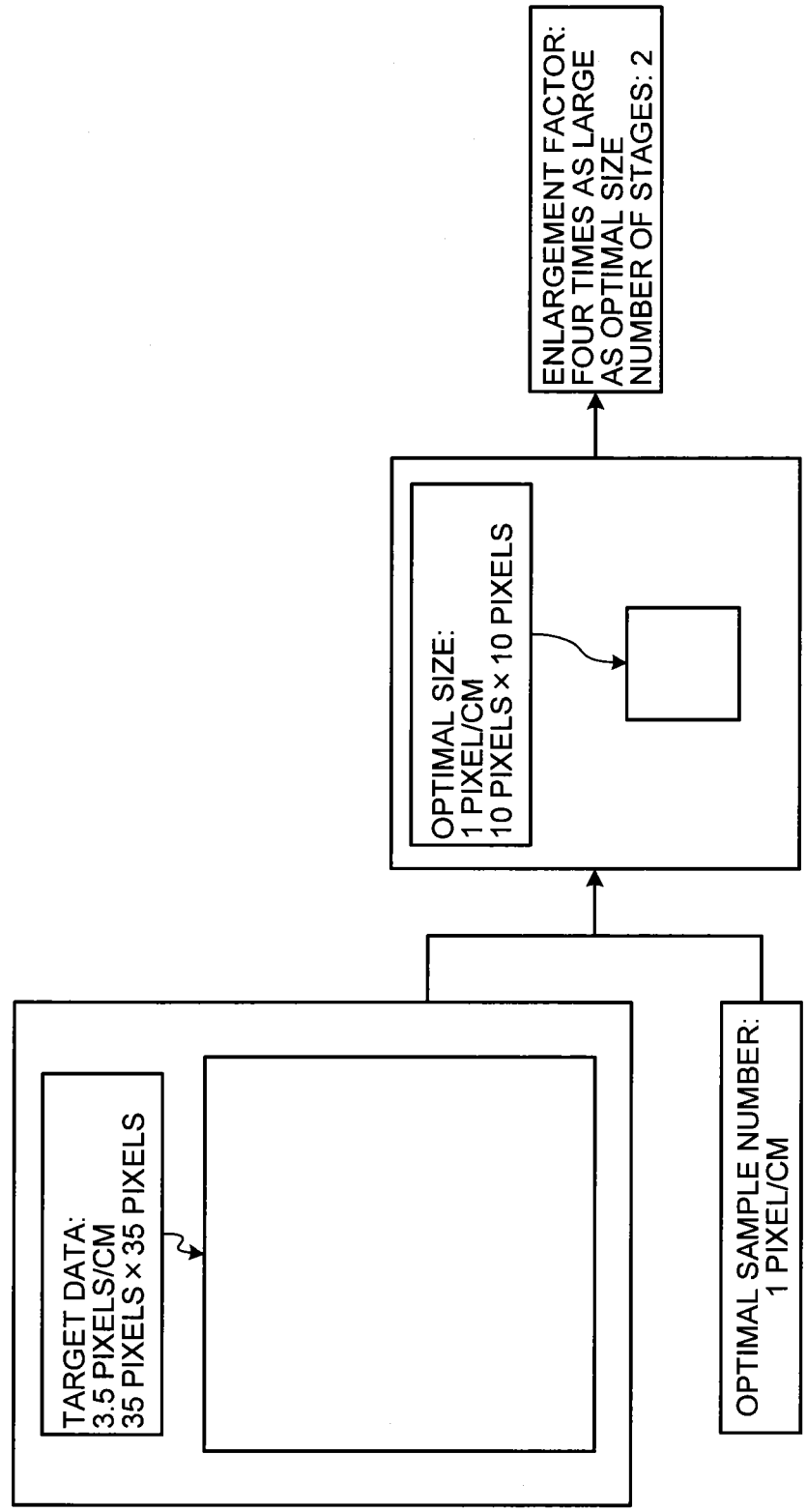

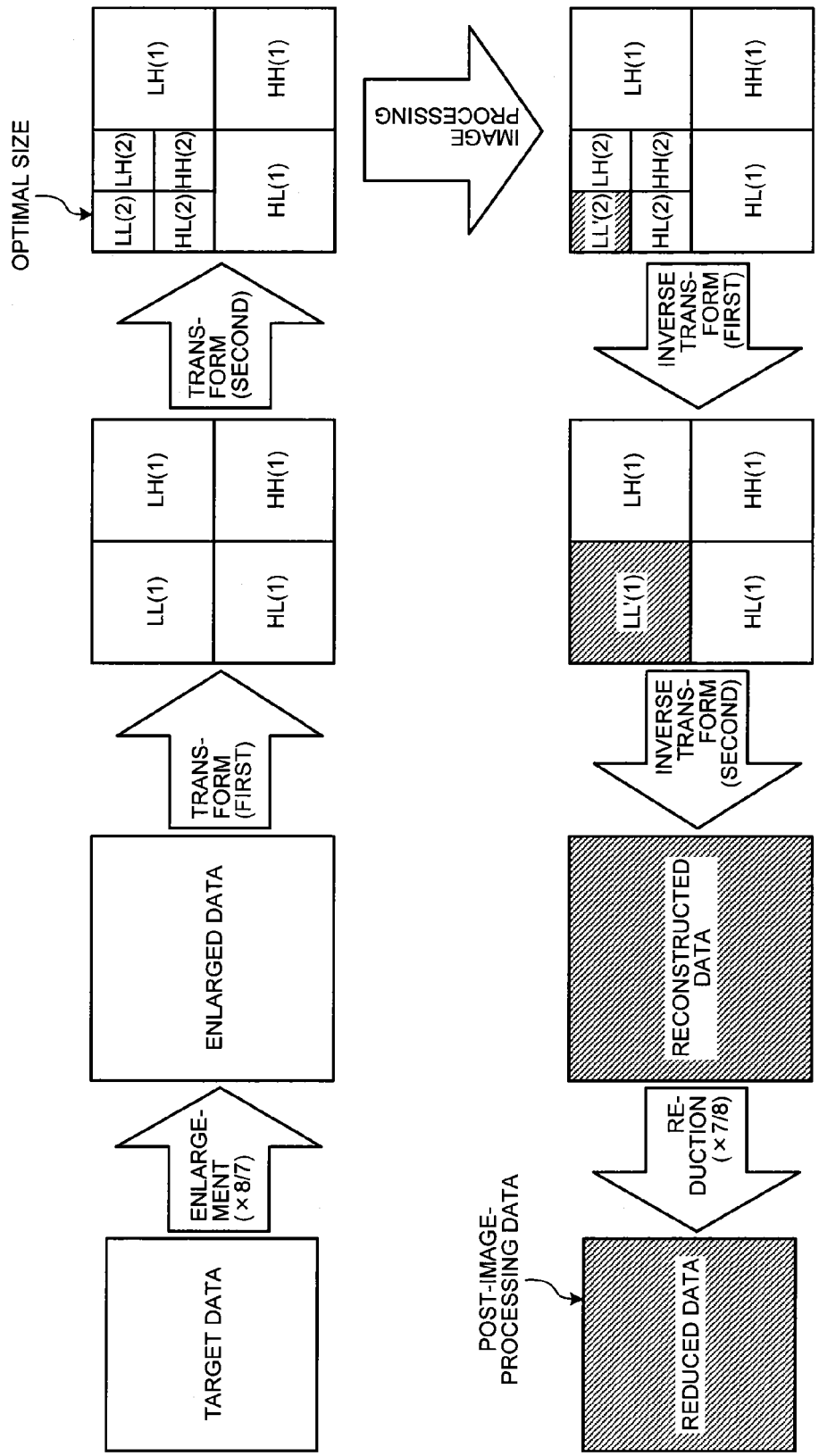

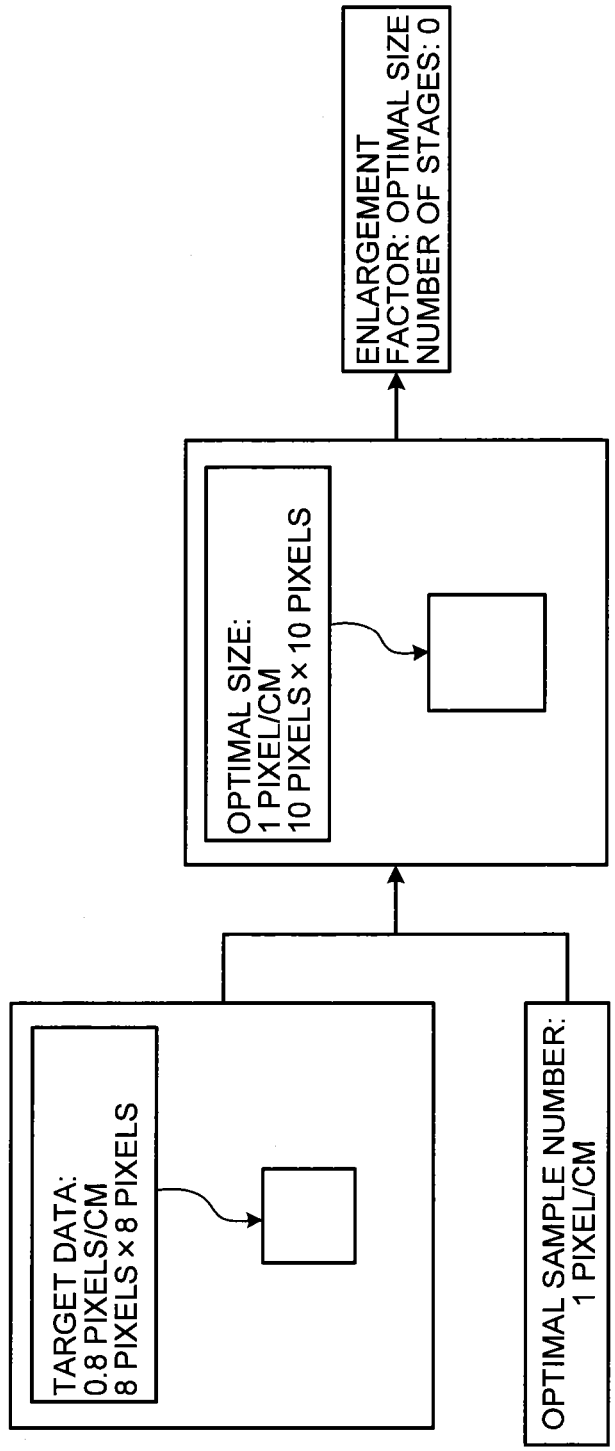

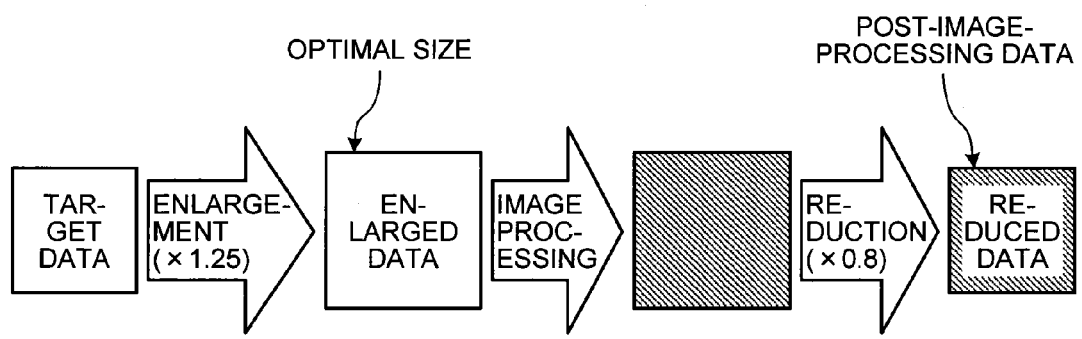

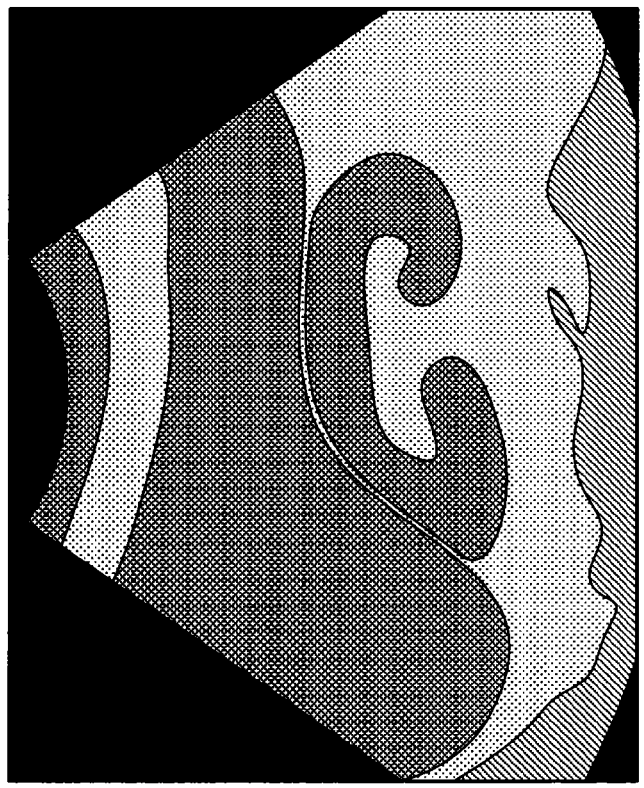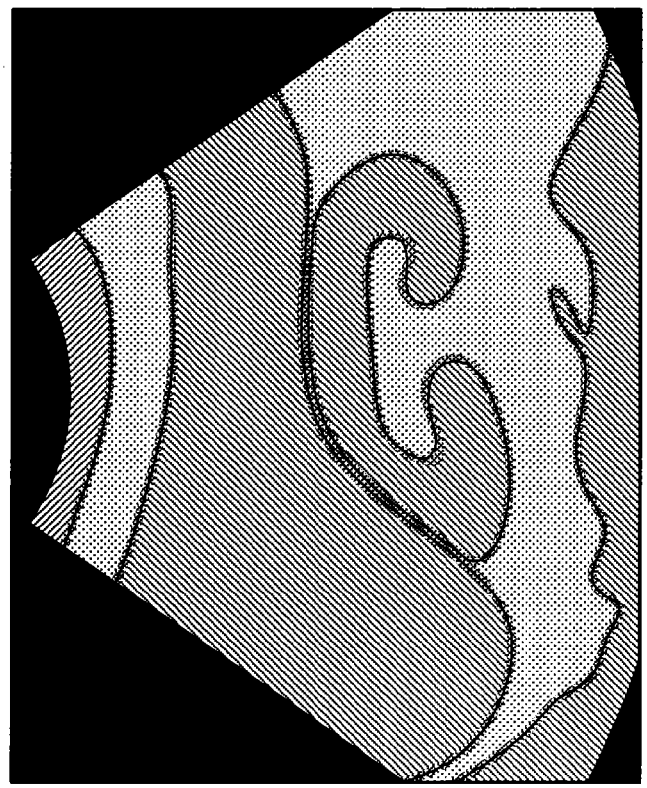
FIG.11

FIG.14A

| IMAGE PROCESSING | OPTIMAL SAMPLE NUMBER | |
|---|---|---|
| A | TRANSMISSION AND RECEPTION CONDITION 1 | a1 |
| | TRANSMISSION AND RECEPTION CONDITION 2 | a2 |
| | TRANSMISSION AND RECEPTION CONDITION 3 | a3 |
| | ⋮ | ⋮ |

FIG.14B

| IMAGE PROCESSING | OPTIMAL SAMPLE NUMBER | |
|---|---|---|
| A | ORGAN 1 | a1' |
| | ORGAN 2 | a2' |
| | ORGAN 3 | a3' |
| | ⋮ | ⋮ |

FIG.14C

| IMAGE PROCESSING | OPTIMAL SAMPLE NUMBER | | |
|---|---|---|---|
| A | ORGAN 1 | TRANSMISSION AND RECEPTION CONDITION 1 | a11 |
| | | TRANSMISSION AND RECEPTION CONDITION 2 | a12 |
| | | TRANSMISSION AND RECEPTION CONDITION 3 | a13 |
| | | ⋮ | ⋮ |
| | ⋮ | ⋮ | ⋮ |
| ⋮ | ⋮ | ⋮ | ⋮ |

…

IMAGE PROCESSING APPARATUS AND MEDICAL IMAGE DIAGNOSIS APPARATUS

CROSS-REFERENCE TO RELATED APPLICATIONS

This application is a continuation of PCT international application Ser. No. PCT/JP2012/074081 filed on Sep. 20, 2012 which designates the United States, incorporated herein by reference, and which claims the benefit of priority from Japanese Patent Application No. 2011-205130, filed on Sep. 20, 2011, and Japanese Patent Application No. 2012-207033, filed on Sep. 20, 2012, the entire contents of which are incorporated herein by reference.

FIELD

Embodiments described herein relate generally to an image processing apparatus and a medical image diagnosis apparatus.

BACKGROUND

Conventionally, medical image diagnosis apparatuses such as ultrasound diagnosis apparatuses, X-ray diagnosis apparatuses, X-ray Computed Tomography (CT) apparatuses, and Magnetic Resonance Imaging (MRI) apparatuses are configured to perform various types of image processing processes. Examples of the image processing processes include a filtering process performed for the purpose of smoothing images and reducing noise.

However, the effect of an image processing process varies depending on the actual length per sample in the data serving as a target of the image processing process. For example, between two pieces of image data rendering mutually the same image taking target, if the quantity of pixels per unit length is different, the effect of an image processing process performed on the pieces of image data will also be different.

BRIEF DESCRIPTION OF THE DRAWINGS

FIG. 2 is a drawing for explaining examples of optimal sample numbers used in a process performed by an image processing unit according to the present embodiment;

FIG. 5 and FIG. 6 are drawings for explaining a second example of the image processing process performed by the image processing unit according to the present embodiment;

FIG. 7 and FIG. 8 are drawings for explaining a third example of the image processing process performed by the image processing unit according to the present embodiment;

FIG. 9 is a drawing for explaining an example of parameter settings used for controlling the image processing unit according to the present embodiment;

FIG. 11 is a drawing of comparison examples between a conventional image processing process and an image processing process according to the present embodiment;

FIG. 14A, FIG. 14B, and FIG. 14C are drawings for explaining a second modification example of the optimal sample numbers.

DETAILED DESCRIPTION

An image processing apparatus according to an embodiment includes an enlarging unit, a decomposing unit, a data processing unit, a reconstructing unit, and a reducing unit. The enlarging unit is configured to generate enlarged data by enlarging target data serving as a target of an image processing process, while using an enlargement factor based on an optimal sample number indicating a quantity of samples per unit length that is suitable for the image processing process. The decomposing unit is configured to generate a group of data satisfying the optimal sample number by performing a decomposing process on the enlarged data, the decomposing process being realized by a multi-resolution analysis having a predetermined number of stages based on the enlargement factor. The data processing unit is configured to generate an already-processed group of data by performing the image processing process on the group of data satisfying the optimal sample number. The reconstructing unit is configured to generate reconstructed data by performing a reconstructing process realized by a multi-resolution analysis having the predetermined number of stages on the already-processed group of data. The reducing unit is configured to generate reduced data by reducing the reconstructed data in such a manner that a quantity of samples per unit length becomes equal to a quantity of samples per unit length in the target data.

In the following sections, exemplary embodiments of an image processing apparatus will be explained in detail, with reference to the accompanying drawings. An ultrasound diagnosis apparatus having functions of the image processing apparatus will be explained as the exemplary embodiments.

Figure 1:
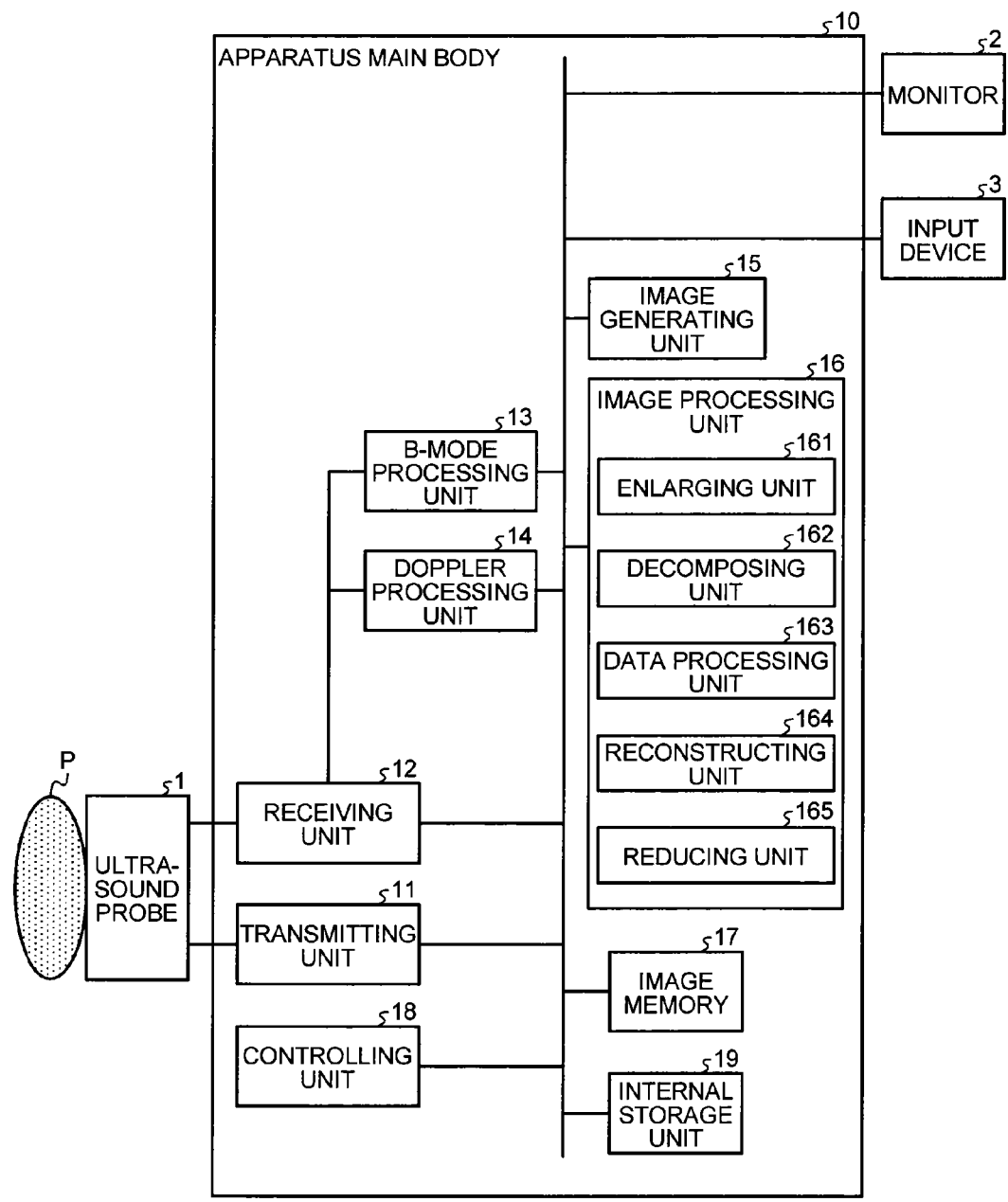
FIG. 1 is a drawing for explaining an exemplary configuration of an ultrasound diagnosis apparatus according to a present embodiment.

First, a configuration of an ultrasound diagnosis apparatus according to an exemplary embodiment will be explained. FIG. 1 is a drawing for explaining an exemplary configuration of the ultrasound diagnosis apparatus according to the present embodiment. As shown in FIG. 1, the ultrasound diagnosis apparatus according to the present embodiment includes an ultrasound probe 1, a monitor 2, an input device 3, and an apparatus main body 10.

The ultrasound probe 1 includes a plurality of piezoelectric transducer elements, which generate an ultrasound wave based on a drive signal supplied from a transmitting unit 11 included in the apparatus main body 10 (explained later). Further, the ultrasound probe 1 receives a reflected wave from a subject P and converts the received reflected wave into an electric signal. Further, the ultrasound probe 1 includes matching layers included in the piezoelectric transducer elements, as well as a backing material that prevents ultrasound waves from propagating rearward from the piezoelectric transducer elements. The ultrasound probe 1 is detachably connected to the apparatus main body 10.

When an ultrasound wave is transmitted from the ultrasound probe 1 to the subject P, the transmitted ultrasound wave is repeatedly reflected on a surface of discontinuity of acoustic impedances at a tissue in the body of the subject P and is received as a reflected-wave signal by the plurality of piezoelectric transducer elements included in the ultrasound probe 1. The amplitude of the received reflected-wave signal is dependent on the difference between the acoustic impedances on the surface of discontinuity on which the ultrasound wave is reflected. When the transmitted ultrasound pulse is reflected on the surface of a flowing bloodstream or a cardiac wall, the reflected-wave signal is, due to the Doppler effect, subject to a frequency shift, depending on a velocity component of the moving objects with respect to the ultrasound wave transmission direction.

It should be noted that the present embodiment is applicable to a situation where the ultrasound probe 1 is an ultrasound probe configured to scan the subject P two-dimensionally and to a situation where the ultrasound probe 1 is an ultrasound probe configured to scan the subject P three-dimensionally, while using the ultrasound waves. An example of the ultrasound probe 1 configured to scan the subject P three-dimensionally is a mechanical scan probe that scans the subject P three-dimensionally by causing a plurality of ultrasound transducer elements which scans the subject P two-dimensionally to swing at a predetermined angle (a swinging angle). Another example of the ultrasound probe 1 configured to scan the subject P three-dimensionally is a two-dimensional ultrasound probe (a 2D probe) that performs an ultrasound scan on the subject P three-dimensionally by using a plurality of ultrasound transducer elements that are arranged in a matrix formation. The 2D probe is also able to scan the subject P two-dimensionally by transmitting the ultrasound waves in a converged manner.

The input device 3 includes a mouse, a keyboard, a button, a panel switch, a touch command screen, a foot switch, a trackball, a joystick, and the like. The input device 3 receives various types of setting requests from an operator of the ultrasound diagnosis apparatus and transfers the received various types of setting requests to the apparatus main body 10.

The monitor 2 displays a Graphical User Interface (GUI) used by the operator of the ultrasound diagnosis apparatus to input the various types of setting requests through the input device 3 and displays an ultrasound image and the like generated by the apparatus main body 10.

The apparatus main body 10 is an apparatus that generates the ultrasound image based on the reflected wave received by the ultrasound probe 1. As shown in FIG. 1, the apparatus main body 10 includes the transmitting unit 11, a receiving unit 12, a B-mode processing unit 13, a Doppler processing unit 14, an image generating unit 15, an image processing unit 16, an image memory 17, a controlling unit 18, and an internal storage unit 19.

The transmitting unit 11 includes a trigger generating circuit, a transmission delaying circuit, a pulser circuit, and the like and supplies the drive signal to the ultrasound probe 1. The pulser circuit repeatedly generates a rate pulse for forming a transmission ultrasound wave at a predetermined rate frequency. Further, the transmission delaying circuit applies a delay time that is required to converge the ultrasound wave generated by the ultrasound probe 1 into the form of a beam and to determine transmission directionality and that corresponds to each of the piezoelectric transducer elements, to each of the rate pulses generated by the pulser circuit. Further, the trigger generating circuit applies a drive signal (a drive pulse) to the ultrasound probe 1 with timing based on the rate pulses. In other words, the delaying circuit arbitrarily adjusts the directions of the transmissions from the surface of piezoelectric transducer elements, by varying the delay times applied to the rate pulses.

The transmitting unit 11 has a function to be able to instantly change the transmission frequency, the transmission drive voltage, and the like, for the purpose of executing a predetermined scanning sequence based on an instruction from the controlling unit 18 (explained later). In particular, the configuration to change the transmission drive voltage is realized by using a linear-amplifier-type transmitting circuit of which the value can be instantly switched or by using a mechanism configured to electrically switch between a plurality of power source units.

The receiving unit 12 includes an amplifier circuit, an Analog/Digital (A/D) converter, an adder, a phase detecting circuit, and the like and generates reflected-wave data by performing various types of processes on the reflected-wave signal received by the ultrasound probe 1. The amplifier circuit amplifies the reflected-wave signal for each of channels and performs a gain correcting process thereon. The A/D converter applies an A/D conversion to the gain-corrected reflected-wave signal and applies a delay time required to determine reception directionality to digital data. The adder performs an adding process on the reflected-wave signals processed by the A/D converter. As a result of the adding process performed by the adder, reflected components from the direction corresponding to the reception directionality of the reflected-wave signals are emphasized. The phase detecting circuit converts an output signal from the adder into an In-phase signal ("I signal") and Quadrature-phase signal ("Q signal") in a baseband bandwidth. Further, the phase detecting circuit outputs the I signal and the Q signal (hereinafter, "IQ signals") to a processing unit at the subsequent stage. The data prior to the process performed by the phase detecting circuit may be referred to as a "Radio Frequency (RF) signal". In the following sections, "the IQ signals and the RF signal" generated based on the reflected wave of the ultrasound wave will be collectively referred to as "reflected-wave data".

In this manner, the transmitting unit 11 and the receiving unit 12 control the transmission directionality and the reception directionality in the transmission and the reception of the ultrasound wave.

In this situation, if the ultrasound probe 1 is configured to be able to perform a three-dimensional scan, the transmitting unit 11 and the receiving unit 12 are each able to also cause a three-dimensional ultrasound beam to be transmitted from the ultrasound probe 1 to the subject P, so that three-dimensional reflected-wave data is generated from three-dimensional reflected-wave signals received by the ultrasound probe 1.

The B-mode processing unit 13 receives the reflected-wave data from the receiving unit 12 and generates data (B-mode data) in which the strength of each signal is expressed by a degree of brightness, by performing a logarithmic amplification, an envelope detection process, and the like on the received reflected-wave data.

The Doppler processing unit 14 extracts bloodstreams, tissues, and contrast echo components under the influence of the Doppler effect by performing a frequency analysis so as to obtain velocity information from the reflected-wave data received from the receiving unit 12, and further generates data (Doppler data) obtained by extracting moving object information such as an average velocity, the dispersion, the power, and the like for a plurality of points.

The B-mode processing unit 13 and the Doppler processing unit 14 according to the present embodiment are able to process both two-dimensional reflected-wave data and three-dimensional reflected-wave data. In other words, the B-mode processing unit 13 is able to generate two-dimensional B-mode data from two-dimensional reflected-wave data and is also able to generate three-dimensional B-mode data from three-dimensional reflected-wave data. The Doppler processing unit 14 is able to generate two-dimensional Doppler data from two-dimensional reflected-wave data and is also able to generate three-dimensional Doppler data from three-dimensional reflected-wave data.

The image generating unit 15 generates ultrasound images based on the reflected wave received by the ultrasound probe 1. In other words, the image generating unit 15 generates ultrasound image data to be output to the monitor 2, from the data generated by the B-mode processing unit 13 and the Doppler processing unit 14. More specifically, from the two-dimensional B-mode data generated by the B-mode processing unit 13, the image generating unit 15 generates B-mode image data in which the strength of the reflected wave is expressed by a degree of brightness. Further, from the two-dimensional Doppler data generated by the Doppler processing unit 14, the image generating unit 15 generates an average velocity image, a dispersion image, and a power image, expressing the moving object information, or Doppler image data, which is an image combining these images.

In this situation, generally speaking, the image generating unit 15 converts (by performing a scan convert process) a scanning line signal sequence from an ultrasound scan into a scanning line signal sequence in a video format used by, for example, television and generates display-purpose ultrasound image data. More specifically, the image generating unit 15 generates the display-purpose ultrasound image data by performing a coordinate transformation process compliant with the ultrasound scanning form used by the ultrasound probe 1. Further, the image generating unit 15 synthesizes text information of various parameters, scale graduations, body marks, and the like with the display-purpose ultrasound image data.

In other words, the B-mode data and the Doppler data are the ultrasound image data before the scan convert process is performed (hereinafter, "pre-scan-convert ultrasound image data"). The data generated by the image generating unit 15 is the display-purpose ultrasound image data obtained after the scan convert process is performed (hereinafter, "post-scan-convert ultrasound image data"). The B-mode data and the Doppler data may also be referred to as raw data.

Further, the image generating unit 15 is also able to generate three-dimensional ultrasound image data. In other words, the image generating unit 15 is also able to generate three-dimensional B-mode image data by performing a coordinate transformation process on the three-dimensional B-mode data generated by the B-mode processing unit 13. The image generating unit 15 is also able to generate three-dimensional color Doppler image data by performing a coordinate transformation process on the three-dimensional Doppler data generated by the Doppler processing unit 14.

Further, the image generating unit 15 is also able to perform various types of rendering processes on three-dimensional ultrasound image data (volume data). More specifically, the image generating unit 15 is able to generate display-purpose two-dimensional ultrasound image data by performing a rendering process on three-dimensional ultrasound image data. An example of the rendering process performed by the image generating unit 15 is a process to reconstruct a Multi Planar Reconstruction (MPR) image by implementing an MPR method. Another example of the rendering process performed by the image generating unit 15 is a Volume Rendering (VR) process to generate a two-dimensional image in which three-dimensional information is reflected.

The image processing unit 16 is a processing unit that performs various types of image processing processes on the ultrasound image data. Further, the image processing unit 16 is also able to perform various types of image processing processes on the reflected-wave data. Examples of the image processing processes performed by the image processing unit 16 include a smoothing process using a Gaussian filter, a median filter, or the like, a noise reducing process using a non-linear anisotropic diffusion filter, or the like, and an edge enhancing process using an edge detecting filter, or the like.

To serve as a processing unit that performs such processes, the image processing unit 16 includes an enlarging unit 161, a decomposing unit 162, a data processing unit 163, a reconstructing unit 164, and a reducing unit 165, as shown in FIG. 1. The enlarging unit 161 is a processing unit that performs an enlarging process on target data serving as a target of an image processing process. The decomposing unit 162 is a processing unit that decomposes the data output from the enlarging unit 161 into a group of data made up of low-frequency component data (low-frequency decomposed image data) and data (high-frequency decomposed image data) including high-frequency components, by performing a multi-resolution analysis.

Further, the data processing unit 163 is a processing unit that performs the various types of image processing processes described above on a part or all of the data output from the decomposing unit 162. Further, the reconstructing unit 164 is a processing unit that performs a reconstructing process to synthesize together the data output from the data processing unit 163 and the data output from the decomposing unit 162 or to synthesize together the group of data output from the data processing unit 163, by performing a multi-resolution analysis. The reducing unit 165 is a processing unit that performs a reducing process on the data output from the reconstructing unit 164.

In the present embodiment, an example will be explained in which the decomposing unit 162 performs a wavelet transform as the decomposing process realized by the multi-resolution analysis, whereas the reconstructing unit 164 performs a wavelet inverse transform as the reconstructing process realized by the multi-resolution analysis. It should be noted, however, that the present embodiment is also applicable to a situation where the decomposing unit 162 and the reconstructing unit 164 perform a multi-resolution decomposition and a multi-resolution reconstruction, respectively, by implementing a Laplacian pyramid method.

Further, the ultrasound image data used as a processing target by the image processing unit 16 may be the raw data generated by the B-mode processing unit 13 and the Doppler processing unit 14 or may be the display-purpose ultrasound image data generated by the image generating unit 15. Also, the reflected-wave data used as a processing target by the image processing unit 16 may be the RF signal or may be the IQ signals. In other words, the target data used as a processing target by the image processing unit 16 is data generated based on the reflected wave of the ultrasound wave and may be any of the following: "pre-scan-convert ultrasound image data"; "post-scan-convert ultrasound image data"; "reflected-wave data prior to a wave detecting process"; and "reflected-wave data after a wave detecting process". Processes performed by the image processing unit 16 according to the present embodiment will be explained later.

The image memory 17 is a memory for storing therein the ultrasound image data generated by the image generating unit 15 and processing results of the image processing unit 16. Further, the image memory 17 is also able to store therein the raw data generated by the B-mode processing unit 13 and the Doppler processing unit 14. The image memory 17 is also able to store therein the RF signal and the IQ signals.

The internal storage unit 19 stores therein various types of data such as a control computer program (hereinafter, "control program") to realize ultrasound transmissions and receptions, image processing, and display processing, as well as diagnosis information (e.g., patients' IDs, medical doctors' observations), diagnosis protocols, and various types of body marks. Further, the internal storage unit 19 may be used, as necessary, for storing therein any of the images stored in the image memory 17. Furthermore, the data stored in the internal storage unit 19 can be transferred to any external peripheral device via an interface circuit (not shown).

The controlling unit 18 is a controlling processor (a Central Processing Unit (CPU)) that realizes functions of an information processing apparatus and is configured to control the entire processes performed by the ultrasound diagnosis apparatus. More specifically, based on the various types of setting requests input by the operator via the input device 3 and various types of control programs and various types of data read from the internal storage unit 19, the controlling unit 18 controls processes performed by the transmitting unit 11, the receiving unit 12, the B-mode processing unit 13, the Doppler processing unit 14, the image generating unit 15, and the image processing unit 16. Further, the controlling unit 18 exercises control so that the monitor 2 displays the ultrasound image data stored in the image memory 17 and the various types of image data stored in the internal storage unit 19, or a GUI used for realizing the processes performed by the image processing unit 16 and the processing results of the image processing unit 16, and the like.

An overall configuration of the ultrasound diagnosis apparatus according to the present embodiment has thus been explained. The ultrasound diagnosis apparatus according to the present embodiment configured as described above captures an ultrasound image by performing an ultrasound transmission and reception. Further, the ultrasound diagnosis apparatus according to the present embodiment performs various types of image processing processes in response to, for example, an instruction from the operator. However, the effect of an image processing process varies, if the actual length per sample in the data serving as a target of the image processing process is different. For example, between two pieces of image data rendering mutually the same image taking target, if the quantity of pixels per unit length is different, the effect of an image processing process performed on the pieces of image data will also be different.

To cope with this situation, the ultrasound diagnosis apparatus according to the present embodiment executes the processes performed by the image processing unit 16 explained in detail below, for the purpose of optimizing the effect of each image processing process. In other words, the enlarging unit 161 generates enlarged data by enlarging target data serving as a target of an image processing process while using an enlargement factor based on an optimal sample number indicating the quantity of samples per unit length that is suitable for the image processing process. More specifically, the enlarging unit 161 generates the enlarged data while using such an enlargement factor that causes the quantity of samples per unit length in the target data to be a power of 2 of the optimal sample number. Further, the decomposing unit 162 generates a group of data satisfying the optimal sample number by performing a decomposing process on the enlarged data, the decomposing process being realized by a multi-resolution analysis having a predetermined number of stages based on the enlargement factor. The group of data includes low-frequency component data that satisfies the optimal sample number. Further, the data processing unit 163 generates an already-processed group of data by performing the image processing process on the group of data satisfying the optimal sample number. In the present embodiment, the data processing unit 163 generates already-processed low-frequency component data by performing the image processing process on the low-frequency component data satisfying the optimal sample number.

Further, the reconstructing unit 164 generates reconstructed data by performing a reconstructing process realized by a multi-resolution analysis having the predetermined number of stages on the already-processed group of data. In the present embodiment, the reconstructing unit 164 generates the reconstructed data by performing the reconstructing process realized by the multi-resolution analysis having the predetermined number of stages, while using the already-processed low-frequency component data and a group of data including high-frequency components generated as a result of the decomposing process realized by the multi-resolution analysis performed by the decomposing unit 162. Further, the reducing unit 165 generates reduced data by reducing the reconstructed data in such a manner that the quantity of samples per unit length becomes equal to the quantity of samples per unit length in the target data.

In the following sections, a specific example of the image processing process described above performed by the image processing unit 16 will be explained in detail with reference to FIG. 2 and the like. FIG. 2 is a drawing for explaining examples of optimal sample numbers used in a process performed by the image processing unit according to the present embodiment.

For example, as shown in FIG. 2, the internal storage unit 19 stores therein a table that has registered therein an "optimal sample number" for each of different types of image processing processes, the "optimal sample numbers" each indicating the quantity of samples per unit length that optimizes the effect of the corresponding image processing process. In the examples shown in FIG. 2, the internal storage unit 19 stores therein, in a table format, information indicating that the optimal sample number for an image processing process "A" is "a", that the optimal sample number for an image processing process "B" is "b", and that the optimal sample number for an image processing process "C" is "c", when the target data is post-scan-convert ultrasound image data. In this situation, "the optimal sample number: a" indicates that, with respect to the post-scan-convert ultrasound image data, the effect of the image processing process "A" is optimized when the target object having a size of 1 centimeter is rendered with pixels of which the quantity is "a". The table illustrated in FIG. 2 is registered by, for example, an operator or an administrator of the ultrasound diagnosis apparatus.

If the values of optimal sample numbers are different between the situation where the target data is pre-scan-convert ultrasound image data and the situation where the target data is post-scan-convert ultrasound image data, the operator or the administrator of the ultrasound diagnosis apparatus registers an "optimal sample number" for each of the different types of image processing process, for each of the different types of ultrasound image data.

Further, the controlling unit 18 obtains the optimal sample number corresponding to the type of the target data and the type of the image processing process specified by the operator, by referring to the table stored in the internal storage unit 19. An arrangement is acceptable in which the optimal sample numbers are manually input by the operator via the input device 3.

In the following sections, an example will be explained in which the operator has specified the image processing process "A" that is a filtering process to apply a smoothing process to post-scan-convert ultrasound image data. Also, in the following explanation, it is assumed that the optimal sample number "a" for the image processing process "A" denotes "one pixel per centimeter (1 pixel/cm)".

First, the controlling unit 18 obtains "the optimal sample number: 1 pixel/cm" by referring to the table stored in the internal storage unit 19. Further, the controlling unit 18 obtains information indicating "post-scan-convert ultrasound image data" specified by the operator as the target data. More specifically, the controlling unit 18 obtains, as the information about the target data, the "quantity of samples (pixels) per unit length" and the "size" of the "post-scan-convert ultrasound image data" specified by the operator. For example, the controlling unit 18 obtains the information about the target data from ultrasound transmission and reception conditions and from display settings of the ultrasound image specified by the operator.

Further, the controlling unit 18 controls processes to be performed by the image processing unit 16 by determining an enlargement factor of the enlarging process to be performed by the enlarging unit 161 and the number of stages of the multi-resolution analyses to be performed by the decomposing unit 162 and the reconstructing unit 164, based on the optimal sample number and the information about the target data. In the following sections, the processes performed by the controlling unit 18 and the image processing unit 16 will be explained by sequentially using a "first example", a "second example", and a "third example" that involve mutually different pieces of information about the target data.

Figure 3:
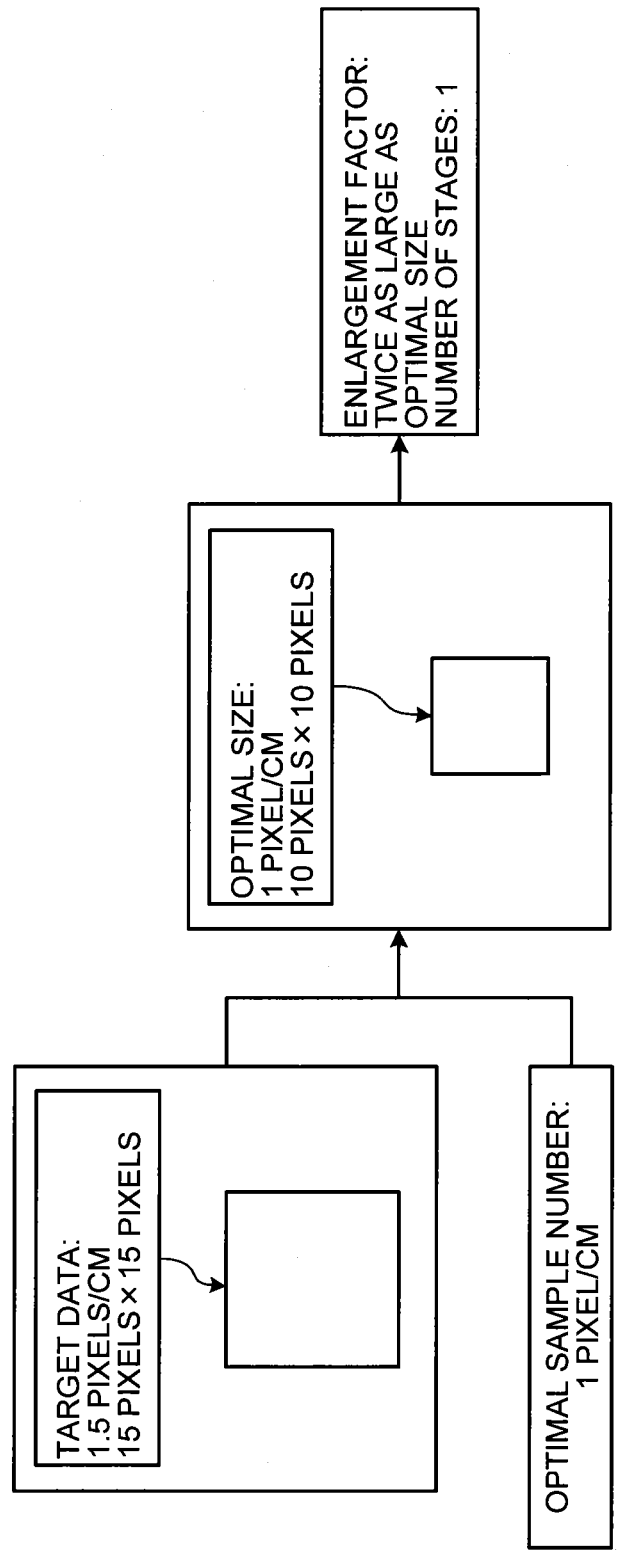
FIG. 3 and FIG. 4 are drawings for explaining a first example of the image processing process performed by the image processing unit according to the present embodiment.
Figure 4:
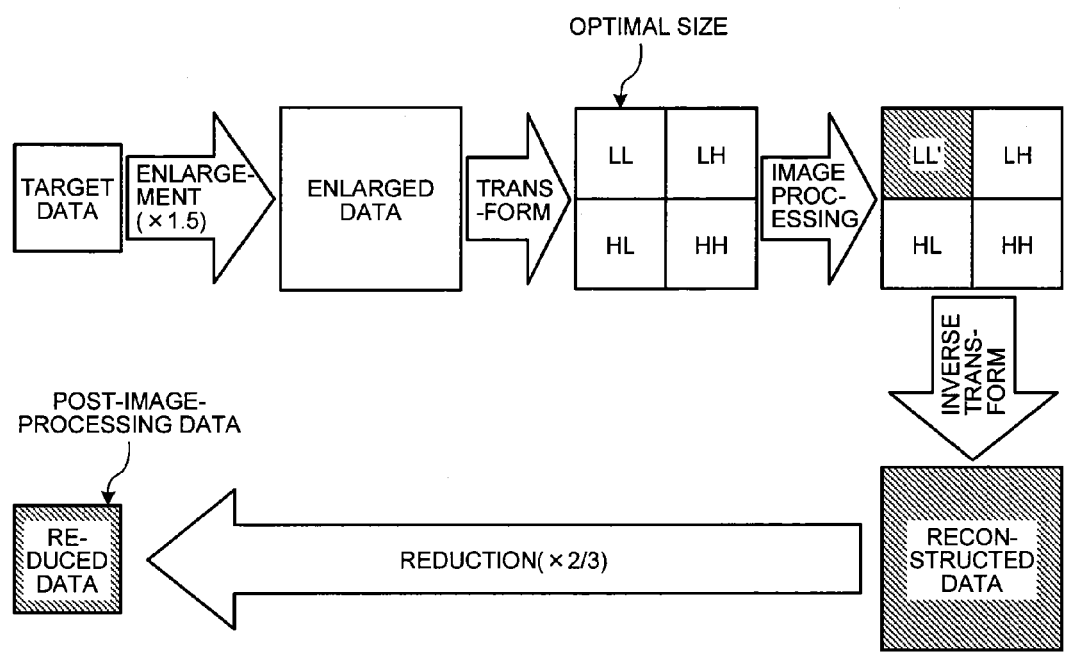

First, the first example will be explained in which the "quantity of samples (pixels) per unit length" of the "post-scan-convert ultrasound image data" serving as the target data is "1.5 pixels per centimeter (1.5 pixels/cm)", whereas the "size" thereof is "15 pixels×15 pixels". FIGS. 3 and 4 are drawings for explaining the first example of the image processing process performed by the image processing unit according to the present embodiment.

As shown in FIG. 3, the controlling unit 18 obtains the information about the target data "1.5 pixels/cm; 15 pixels×15 pixels" and "the optimal sample number: 1 pixel/cm". Further, as shown in FIG. 3, the controlling unit 18 determines that the optimal size that optimizes the effect of the image processing process "A" is "1 pixel/cm; 10 pixels×10 pixels". In this situation, in order to cause the target data currently satisfying "1.5 pixels/cm" to satisfy the optimal sample number "1 pixel/cm", it is necessary to reduce the target data having a size of "15 pixels×15 pixels" to the size of "10 pixels×10 pixels".

Generally speaking, when original data is reduced, high-frequency components thereof are lost. In other words, when target data is reduced to an optimal size, even if an image processing process is performed on the reduced data, it is not possible to optimize the effect of the image processing process.

Generally speaking, in contrast, when original data is enlarged, information of the original data is maintained. Further, in a multi-resolution analysis used for a data compression or the like, it is possible to generate data having half the height and width of the original data by performing a decomposing process, and it is further possible to restore (reconstruct) data having substantially the same information as the pre-decomposition data by using the decomposed data. Furthermore, low-frequency component data (low-frequency decomposed image data) generated from the decomposing process realized by the multi-resolution analysis is considered to maintain information approximating that of the pre-decomposition data.

For this reason, according to the present embodiment, the decomposing process and the reconstructing process realized by the multi-resolution analyses are performed as a pre-processing process and a post-processing process of the image processing process. As mentioned above, as a result of the decomposing process realized by the multi-resolution analysis, the height and width of the decomposed data are each half the height and width of the pre-decomposition data. Accordingly, in the present embodiment, enlarged data is obtained by enlarging the target data while using such "an enlargement factor that causes" the quantity of samples per unit length in the target data to be "'2$^n$'" times as large as the optimal sample number", and subsequently, the low-frequency component data satisfying the optimal number is obtained by performing the decomposing process realized by the multi-resolution analysis having "n" stages on the obtained enlarged data.

In other words, the controlling unit 18 determines the parameter "n" used for controlling the process performed by the image processing unit 16, based on the optimal sample number and the information about the target data. In the first example where the optimal size is "1 pixel/cm; 10 pixels×10 pixels", whereas the target data is ultrasound image data satisfying "1.5 pixels/cm; 15 pixels×5 pixels", the data that is "twice as large as the optimal size" should satisfy "2 pixels/cm". In other words, in order to cause the target data currently satisfying "1.5 pixels/cm" to satisfy "2 pixels/cm", it is necessary to perform an enlarging process thereon. Accordingly, in the first example, the controlling unit 18 determines that the parameter should be "n=1" as shown in FIG. 3, i.e., "the enlargement factor: twice as large as the optimal size; the number of stages: 1".

Further, in the first example, the image processing unit 16 performs the process shown in FIG. 4, under the control of the controlling unit 18. First, the enlarging unit 161 generates enlarged data by causing the target data (the ultrasound image data) currently having the size of "15 pixels×15 pixels" to have a size of "20 pixels×20 pixels", which is "twice as large as the optimal size". In other words, as shown in FIG. 4, the enlarging unit 161 generates the enlarged data in which the quantity of samples per unit length is twice as large as the optimal sample number, by enlarging the ultrasound image data while using an enlargement factor of "1.5". Further, as the decomposing process realized by the multi-resolution analysis, the decomposing unit 162 performs one stage of wavelet transform. As a result, as shown in FIG. 4, the decomposing unit 162 decomposes the enlarged data into "LL" which is low-frequency component data and "HL, LH, and HH", which is a group of data including high-frequency component data.

In this situation, "LL" is a piece of data in which the components in both the horizontal direction and the vertical direction are low-frequency components. "HL" is a piece of data in which the component in the horizontal direction is a high-frequency component, whereas the component in the vertical direction is a low-frequency component. "LH" is a piece of data in which the component in the horizontal direction is a low-frequency component, whereas the component in the vertical direction is a high-frequency component. "HH" is a piece of data in which the components in both the horizontal direction and the vertical direction are high-frequency components. The data "LL" shown in FIG. 4 is low-frequency component data having the optimal size. By performing the image processing process "A" on the data "LL", the data processing unit 163 generates already-processed low-frequency component data (see "LL'" shown in FIG. 4).

Further, by performing one stage of wavelet inverse transform as the reconstructing process realized by the multi-resolution analysis, the reconstructing unit 164 generates reconstructed data by reconstructing "LL', HL, LH, and HH", as shown in FIG. 4. After that, the reducing unit 165 generates reduced data by reducing the reconstructed data in such a manner that the quantity of samples per unit length becomes equal to the quantity of samples per unit length in the target data. In other words, as shown in FIG. 4, the reducing unit 165 generates the reduced data by reducing the reconstructed data while using a reduction factor of "⅔". Further, the reducing unit 165 stores the reduced data into the image memory 17, as post-image-processing data obtained by performing the image processing process "A" on the target data. For example, the controlling unit 18 has the post-image-processing data displayed on the monitor 2.

Next, the second example will be explained in which the "quantity of samples (pixels) per unit length" of the "post-scan-convert ultrasound image data" serving as the target data is "3.5 pixels per centimeter (3.5 pixels/cm)", whereas the "size" thereof is "35 pixels×35 pixels". FIGS. 5 and 6 are drawings for explaining the second example of the image processing process performed by the image processing unit according to the present embodiment.

As shown in FIG. 5, having obtained information about the target data "3.5 pixels/cm; 35 pixels×35 pixels" and "the optimal sample number: 1 pixel/cm", the controlling unit 18 determines that the optimal size is "1 pixel/cm; 10 pixels×10 pixels". In other words, as shown in FIG. 5, the controlling unit 18 determines that, in order to optimize the effect of the image processing process "A", it is necessary to enlarge the target data and to generate low-frequency component data satisfying "1 pixel/cm; 10 pixels×10 pixels".

In this situation, the data that is "twice as large as the optimal size" should satisfy "2 pixels/cm". In other words, in order to cause the target data currently satisfying "3.5 pixels/cm" to satisfy "2 pixels/cm", it is necessary to perform a reducing process thereon. In contrast, the data that is "four times as large as the optimal size" should satisfy "4 pixels/cm". In other words, in order to cause the target data currently satisfying "3.5 pixels/cm" to satisfy "4 pixels/cm", it is necessary to perform an enlarging process thereon. Accordingly, in the second example, the controlling unit 18 determines that the parameter should be "n=2" as shown in FIG. 5, i.e., "the enlargement factor: four times as large as the optimal size; the number of stages: 2".

Further, in the second example, the image processing unit 16 performs the process shown in FIG. 6, under the control of the controlling unit 18. First, the enlarging unit 161 generates enlarged data by causing the target data (the ultrasound image data) currently having the size of "35 pixels×35 pixels" to have a size of "40 pixels×40 pixels", which is "four times as large as the optimal size". In other words, as shown in FIG. 6, the enlarging unit 161 generates the enlarged data in which the quantity of samples per unit length is four times as large as the optimal sample number, by enlarging the ultrasound image data while using an enlargement factor of "8/7". Further, as the decomposing process realized by the multi-resolution analysis, the decomposing unit 162 performs two stages of wavelet transform. In other words, as shown in FIG. 6, by performing a first-stage wavelet transform, the decomposing unit 162 decomposes the enlarged data into "LL(1)" which is first-stage low-frequency component data and "HL(1), LH(1), and HH(1)", which is a first-stage "group of data including high-frequency component data". After that, as shown in FIG. 6, by performing a wavelet transform (second stage) on "LL(1)", the decomposing unit 162 decomposes the data into "LL(2)" which is second-stage low-frequency component data and "HL(2), LH(2), and HH(2)", which is a second-stage "group of data including high-frequency component data".

In this situation, the data "LL(2)" shown in FIG. 6 is low-frequency component data having the optimal size. By performing the image processing process "A" on the data "LL(2)", the data processing unit 163 generates already-processed low-frequency component data (see "LL'(2)" shown in FIG. 6).

Further, the reconstructing unit 164 performs two stages of wavelet inverse transform as the reconstructing process realized by the multi-resolution analysis. In other words, by performing a first-stage wavelet inverse transform, as shown in FIG. 6, the reconstructing unit 164 generates reconstructed data "LL'(1)" by reconstructing "LL'(2), HL(2), LH(2), and HH(2)". Subsequently, by performing a second-stage wavelet inverse transform, the reconstructing unit 164 generates reconstructed data by reconstructing "LL'(1), HL(1), LH(1), and HH(1)". After that, the reducing unit 165 generates reduced data by reducing the reconstructed data in such a manner that the quantity of samples per unit length becomes equal to the quantity of samples per unit length in the target data. In other words, as shown in FIG. 6, the reducing unit 165 generates the reduced data by reducing the reconstructed data while using a reduction factor of "⅞". Further, the reducing unit 165 stores the reduced data into the image memory 17, as post-image-processing data obtained by performing the image processing process "A" on the target data. For example, the controlling unit 18 has the post-image-processing data displayed on the monitor 2.

Next, the third example will be explained in which the "quantity of samples (pixels) per unit length" of the "post-scan-convert ultrasound image data" serving as the target data is "0.8 pixels per centimeter (0.8 pixels/cm)", whereas the "size" thereof is "8 pixels×8 pixels". FIGS. 7 and 8 are drawings for explaining the third example of the image processing process performed by the image processing unit according to the present embodiment.

As shown in FIG. 7, having obtained information about the target data "0.8 pixels/cm; 8 pixels×8 pixels" and "the optimal sample number: 1 pixel/cm", the controlling unit 18 determines that the optimal size for performing the image processing process "A" on the target data is "1 pixel/cm; 10 pixels×10 pixels". It should be noted that, in the third example, because it is possible to optimize the effect of the image processing process "A" by enlarging the target data currently satisfying "0.8 pixels/cm" so as to satisfy "1 pixel/cm", the controlling unit 18 determines that "no wavelet transform is required".

Accordingly, in the third example, the controlling unit 18 determines that the parameter should be "n=0" as shown in FIG. 7, i.e., "the enlargement factor: the optimal size; the number of stages: 0". In other words, when the quantity of samples per unit length in the target data is equal to or smaller than the optimal sample number, the image processing unit 16 performs the image processing process without employing the functions of the decomposing unit 162 and the reconstructing unit 164.

More specifically, the enlarging unit 161 generates enlarged data by enlarging the target data while using an enlargement factor that causes the quantity of samples per unit length in the target data to be equal to the optimal sample number. In the third example shown in FIG. 8, the enlarging unit 161 generates the enlarged data by causing the target data (the ultrasound image data) currently having the size of "8 pixels×8 pixels" to have a size of "10 pixels×10 pixels", which is "the optimal size". In other words, as shown in FIG. 8, the enlarging unit 161 generates the enlarged data in which the quantity of samples per unit length is the optimal sample number by enlarging the ultrasound image data while using an enlargement factor of "1.25". Because the enlarged data shown in FIG. 8 is data having the optimal size, the data processing unit 163 performs the image processing process on the enlarged data. In the third example, the data processing unit 163 performs the image processing process "A" on the enlarged data.

After that, by using the data resulting from the image processing process performed on the enlarged data as a processing target, the reducing unit 165 generates reduced data by reducing the processing target data in such a manner that the quantity of samples per unit length in the processing target data becomes equal to the quantity of samples per unit length in the target data. In other words, as shown in FIG. 8, the reducing unit 165 generates the reduced data by reducing the data resulting from the image processing process while using a reduction factor of "0.8". Further, the reducing unit 165 stores the reduced data into the image memory 17, as post-image-processing data obtained by performing the image processing process "A" on the target data. For example, the controlling unit 18 has the post-image-processing data displayed on the monitor 2.

In the first to the third examples described above, the parameters "n" used for controlling the image processing unit can be summarized as shown in FIG. 9. FIG. 9 is a drawing for explaining an example of parameter settings used for controlling the image processing unit according to the present embodiment. In FIG. 9, the quantity of samples per unit length in the target data is expressed as "S", whereas the optimal sample number is expressed as "So".

First, if "(S/So)≤1" is satisfied, the controlling unit 18 determines, as explained in the third example, that the parameter should be "n=0", as shown in FIG. 9, that the enlargement factor used for generating the enlarged data should be "such an enlargement factor that causes the target data to be equal to ($2^0$ times as large as) the optimal sample number", and that the number of stages for the wavelet transform and inverse transform should be "0", i.e., no wavelet process should be performed. If "(S/So)=1" is satisfied, the enlargement factor used for generating the enlarged data is "1".

In another example, if "1<(S/So)≤2" is satisfied, the controlling unit 18 determines, as explained in the first example, that the parameter should be "n=1", as shown in FIG. 9, that the enlargement factor used for generating the enlarged data should be "such an enlargement factor that causes the target data to be $2^1$ times as large as the optimal sample number", and that the number of stages for the wavelet transform and inverse transform should be "1". If "(S/So)=2" is satisfied, the enlargement factor used for generating the enlarged data is "1".

In yet another example, if "2<(S/So)≤4" is satisfied, the controlling unit 18 determines, as explained in the second example, that the parameter should be "n=2" as shown in FIG. 9, that the enlargement factor used for generating the enlarged data should be "such an enlargement factor that causes the target data to be $2^2$ times as large as the optimal sample number", and that the number of stages for the wavelet transform and inverse transform should be "2". If "(S/So)=4" is satisfied, the enlargement factor used for generating the enlarged data is "1".

In yet another example, if "4<(S/So)≤8" is satisfied, the controlling unit 18 determines that the parameter should be "n=3" as shown in FIG. 9, that the enlargement factor used for generating the enlarged data should be "such an enlargement factor that causes the target data to be $2^3$ times as large as the optimal sample number", and that the number of stages for the wavelet transform and inverse transform should be "3". If "(S/So)=8" is satisfied, the enlargement factor used for generating the enlarged data is "1".

To summarize, except for the third example, if "$2^m-1$<(S/So)≤$2^m$" is satisfied, the controlling unit 18 determines that the parameter should be "n=m" as shown in FIG. 9, that the enlargement factor used for generating the enlarged data should be "such an enlargement factor that causes the target data to be $2^m$ times as large as the optimal sample number", and that the number of stages for the wavelet transform and inverse transform should be "m". If "(S/So)=m" is satisfied, the enlargement factor used for generating the enlarged data is "1".

The present embodiment is also applicable to a situation where, even if "(S/So)≤1" is satisfied, the image processing process is performed by employing the processes of the decomposing unit 162 and the reconstructing unit 164 while using the parameter "n=1". In other words, it is acceptable to configure the present embodiment in such a manner that if "(S/So)≤2" is satisfied, the parameter is set to "n=1". For example, it is acceptable to configure the present embodiment in such a manner that, in the third example described above, the target data is enlarged so as to satisfy "2 pixels/cm", before one stage of wavelet transform, the image processing process, one stage of wavelet inverse transform, and the reducing process are performed.

In the example explained above, the optimal sample number used when the target data is ultrasound image data is the same value for the height direction and for the width direction; however, it is acceptable to configure the present embodiment in such a manner that, when the target data is ultrasound image data, mutually-different optimal sample numbers are used for the height direction and for the width direction. For example, let us discuss a situation where, with respect to the image processing process "A", the optimal sample numbers are set as follows: "the width direction optimal sample number: 1 pixel/cm; and the height direction optimal sample number: 1.5 pixels/cm".

In this situation, in the first example where the target data is data having a size of "15 pixels×15 pixels" and satisfying 1.5 pixels/cm in the width direction and the height direction, the optimal size is "10 pixels×15 pixels" where 1 pixel/cm is satisfied in the width direction and where 1.5 pixels/cm is satisfied in the height direction. Further, enlarged data having a size of "20 pixels×30 pixels" where "2 pixels/cm" is satisfied in the width direction and where "3 pixels/cm" is satisfied in the height direction is obtained by enlarging the target data with an enlargement factor of "3/2" in the width direction and an enlargement factor of "2" in the height direction. The image processing unit 16 generates reconstructed data by performing one stage of wavelet transform, the image processing process, and one stage of wavelet inverse transform on the enlarged data. After that, the image processing unit 16 generates reduced data as post-image-processing data by further reducing the reconstructed data while using a reduction factor of "2/3" in the width direction and a reduction factor of "1/2" in the height direction.

Figure 10:
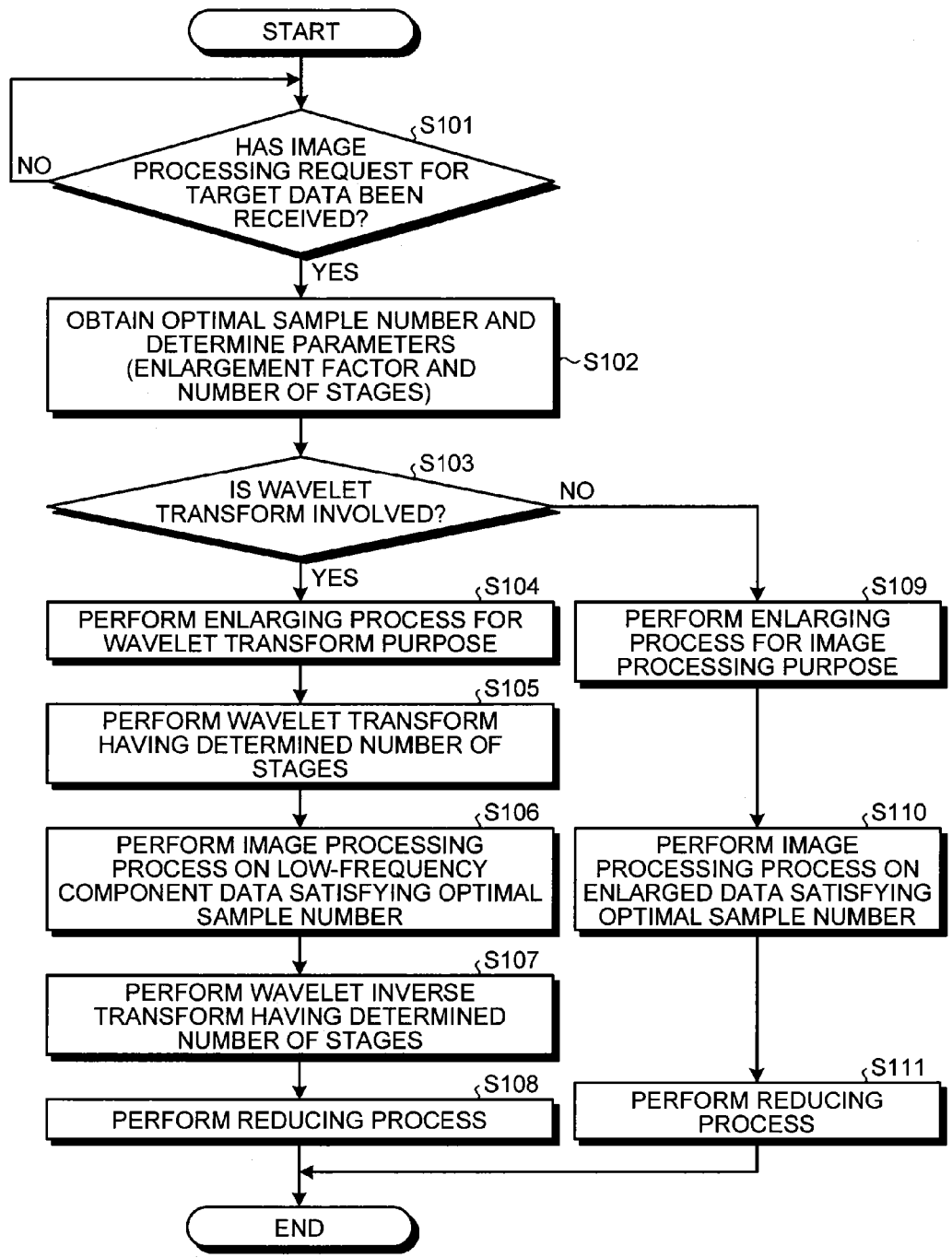
FIG. 10 is a flowchart for explaining an image processing process performed by the ultrasound diagnosis apparatus according to the present embodiment.

Next, a process performed by the ultrasound diagnosis apparatus according to the present embodiment will be explained, with reference to FIG. 10. FIG. 10 is a flowchart for explaining an image processing process performed by the ultrasound diagnosis apparatus according to the present embodiment.

As shown in FIG. 10, the ultrasound diagnosis apparatus according to the present embodiment judges whether an image processing request for the target data has been received (step S101). If no image processing request has been received (step S101: No), the ultrasound diagnosis apparatus goes into a standby state.

On the contrary, when an image processing request for the target data has been received (step S101: Yes), the controlling unit 18 obtains an optimal sample number corresponding to the requested image processing process, together with the information about the target data and determines the parameters (the enlargement factor and the number of stages) to be used in the processes performed by the image processing unit 16 (step S102).

The controlling unit 18 judges whether a wavelet transform is involved or not, based on the determined parameters (step S103).

In this situation, if the controlling unit 18 has determined that the parameter should be "n=0" and that no wavelet transform should be involved because the quantity of samples per unit length in the target data is equal to or smaller than the optimal sample number (step S103: No), the enlarging unit 161 performs an enlarging process to cause the quantity of samples per unit length in the target data to be equal to the optimal sample number, i.e., the enlarging process for an image processing purpose (step S109). After that, the data processing unit 163 performs the image processing process (received at step S101) on the enlarged data satisfying the optimal sample number (step S110). Subsequently, the reducing unit 165 performs a reducing process on the post-image-processing data so as to cause the quantity of samples per unit length to be equal to that in the target data (step S111). The process is thus ended.

On the contrary, if the controlling unit 18 has determined that the parameter "n" should be 1 or larger and that a wavelet transform should be involved because the quantity of samples per unit length in the target data is larger than the optimal sample number (step S103: Yes), the enlarging unit 161 performs an enlarging process for a wavelet transform purpose on the target data (step S104). In other words, the enlarging unit 161 generates enlarged data by enlarging the target data in such a manner that the quantity of samples per unit length is $2^n$ times as large as the optimal sample number.

After that, the decomposing unit 162 performs a wavelet transform having the determined number (n) of stages on the enlarged data (step S105). Also, the data processing unit 163 performs the image processing process (received at step S101) on low-frequency component data satisfying the optimal sample number (step S106).

After that, the reconstructing unit 164 performs a wavelet inverse transform having the determined number (n) of stages by using the already-processed low-frequency data (step S107). Also, the reducing unit 165 performs a reducing process on the reconstructed data generated as a result of the process performed by the reconstructing unit 164, so as to cause the quantity of samples per unit length to be equal to that in the target data (step S108). The process is thus ended. The processes illustrated in FIG. 10 may be performed in a real-time manner during the image taking process of the ultrasound image or may be performed after the image taking process of the ultrasound image.

As explained above, according to the present embodiment, it is possible to optimize the effect of the image processing process by using the multi-resolution analyses and performing the processes in which the optimal sample number is taken into consideration, while avoiding the situation where the target data is directly reduced. FIG. 11 is a drawing of comparison examples between a conventional image processing process and the image processing process according to the present embodiment. The drawing on the left side of FIG. 11 illustrates an example of an ultrasound image that is displayed on the monitor 2 as a result of a conventional image processing process performed without taking the optimal sample number into consideration. The drawing on the right side of FIG. 11 illustrates an example of an ultrasound image that is displayed on the monitor 2 as a result of the image processing process performed while taking the optimal sample number into consideration, as explained in the present embodiment.

As shown on the left side of FIG. 11, according to the conventional method, as a result of performing the image processing process on the target data in which the quantity of samples per unit length does not satisfy the optimal sample number, because the image processing process is not appropriately performed, the entire ultrasound image is in a "blurred" state. On the contrary, as shown on the right side of FIG. 11, when the method according to the present embodiment is used, because the image processing process is performed on the low-frequency component data satisfying the optimal sample number, the image processing process is performed appropriately so that the ultrasound image has sharp image quality.

Further, according to the present embodiment, when the quantity of samples per unit length in the target data is equal to or smaller than the optimal sample number, the image processing process is performed while omitting the decomposing process and the reconstructing process. It is therefore possible to reduce the processing load.

Furthermore, according to the present embodiment, because the wavelet transform and inverse transform are performed as the decomposing and the reconstructing processes realized by the multi-resolution analyses, it is possible to easily optimize the effect of the image processing process by employing the publicly-known technique in a diverted manner.

Figure 12:
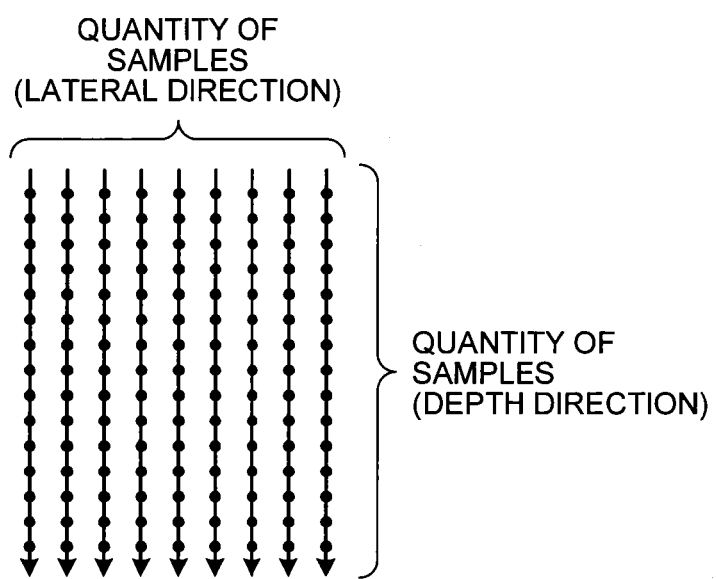
FIG. 12 is a drawing for explaining optimal sample numbers used when target data is reflected-wave data.

Further, as explained above, the present embodiment is also applicable to a situation where the target data is reflected-wave data. FIG. 12 is a drawing for explaining optimal sample numbers used when the target data is reflected-wave data.

When the target data is reflected-wave data, as shown in FIG. 12, the "optimal sample numbers" indicate the quantities of samples in a depth direction and in a lateral direction determined by ultrasound transmission and reception conditions. In this situation, the quantity of samples in the depth direction is a value indicating the quantity of points per unit length at which reflected-wave signals are sampled in the transmission direction of the ultrasound beam. In contrast, the quantity of samples in the lateral direction is a value indicating the quantity of ultrasound beams per unit length that are transmitted in the array direction of the transducer elements.

Accordingly, when the target data is reflected-wave data, a table registering therein the optimal sample numbers for the image processing process "A" has stored therein, for example, "the optimal sample number in the depth direction: $\alpha 1$" and "the optimal sample number in the lateral direction: $\alpha 2$", instead of "the optimal sample number: a" shown in FIG. 2. Further, if the values of optimal sample numbers are different between the situation where the target data is IQ signals and the situation where the target data is RF signals, the operator or the administrator of the ultrasound diagnosis apparatus registers, for example, an "optimal sample number in the depth direction" and an "optimal sample number in the lateral direction" for each of the different types of image processing process, for each of the different types of reflected-wave data.

Further, the controlling unit 18 obtains the quantity of samples per unit length in the reflected-wave data serving as the target data and the optimal sample number corresponding to the image processing process specified for the target data and determines the enlargement factor and the number of stages based on the optimal sample number. Processes are performed by the image processing unit 16 accordingly. In other words, the image processing unit 16 performs an enlarging process, a decomposing process, an image processing process, a reconstructing process, and a reducing process on the reflected-wave data serving as the target data.

If the target data is IQ signals, the image processing unit 16 outputs the reduced data as already-processed reflected-wave data to the B-mode processing unit 13 or to the Doppler processing unit 14. In contrast, if the target data is RF signals, the image processing unit 16 outputs the reduced data to the phase detecting circuit. After that, an output result of the phase detecting circuit is output as already-processed reflected-wave data to the B-mode processing unit 13 or to the Doppler processing unit 14. Subsequently, the B-mode processing unit 13 or the Doppler processing unit 14 generates raw data from the already-processed reflected-wave data, so that the image generating unit 15 generates post-scan-convert ultrasound image data. As explained herein, it is possible to optimize the effect of the image processing process even if the target data is reflected-wave data.

The present embodiment is also applicable to situations where the optimal sample numbers are changed as described in modification examples explained below.

Figure 13A:
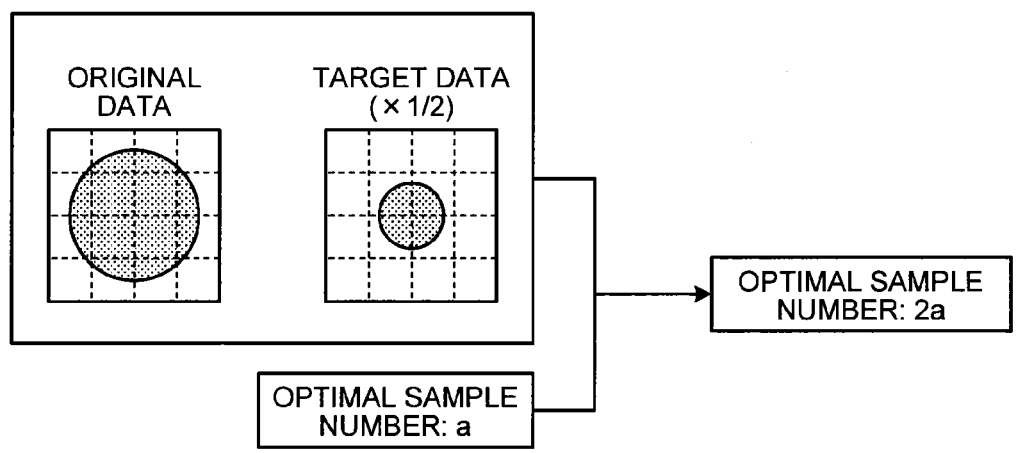
FIG. 13A and FIG. 13B are drawings for explaining a first modification example of the optimal sample numbers.
Figure 13B:
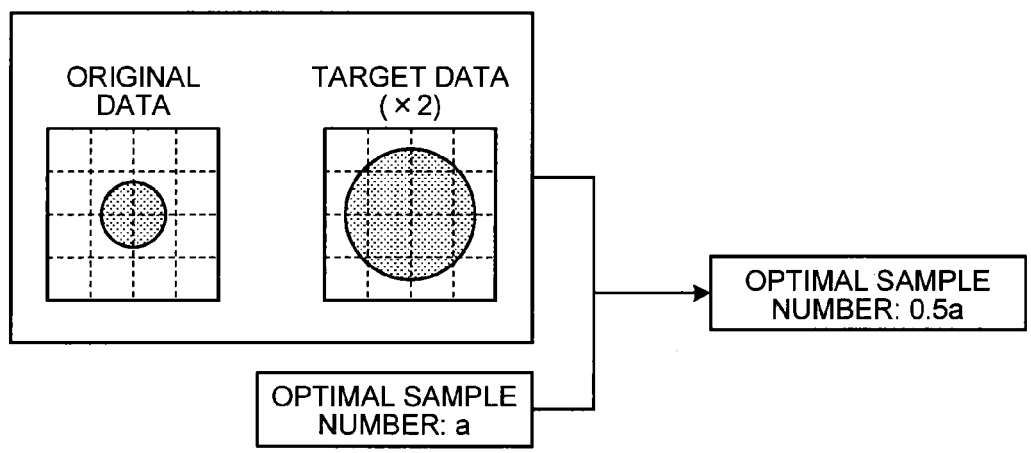

In a first modification example, if the target data has been enlarged or reduced from original data, the optimal sample number is changed according to the enlargement factor or the reduction factor applied to the original data to arrive at the target data. FIGS. 13A and 13B are drawings for explaining the first modification example of the optimal sample numbers.

When the enlargement factor or the reduction factor applied to the original data is different, it means that the length per sample in the target data is also different. For example, when the operator changes the value under "Depth" indicating the length in the depth direction of the ultrasound image, the enlargement factor or the reduction factor is changed. For example, as shown in FIG. 13A, when the operator changes the value under "Depth" to "twice as large" via the input device 3, because the target data is reduced to "½" of the original data, the size of the target object in the original data becomes "½" in the target data. In that situation, the controlling unit 18 obtains the reduction factor "½" and changes "the optimal sample number: a" to "2a", as shown in FIG. 13A.

In another example, as shown in FIG. 13B, when the operator changes the value under "Depth" to "half as large" via the input device 3, because the target data is enlarged to "twice as large" as the original data, the size of the target object in the original data becomes "twice as large" in the target data. In that situation, the controlling unit 18 obtains the enlargement factor "2" and changes "the optimal sample number: a" to "0.5a", as shown in FIG. 13B.

In other words, in the first modification example, if the target data has been enlarged or reduced from the original data, it is possible to optimize the effect of the image processing process performed on the target data, by changing the optimal sample number according to the quantity of samples per unit length in the original data.

In a second modification example, the optimal sample number is changed according to one or both of the ultrasound transmission and reception conditions and the organ serving as an image taking target, as well as according to the type of the image processing process. FIGS. 14A, 14B, and 14C are drawings for explaining the second modification example of the optimal sample numbers.

Even if the type of image processing process is the same, the optimal sample number used for image processing processes may vary depending on the ultrasound transmission and reception conditions such as the rate frequency, the focus position of an ultrasound beam, the scan intervals between ultrasound beams, the quantity of samples in the depth direction, the shape of an ultrasound scan, and the like. To cope with this situation, as shown in FIG. 14A, the operator or the administrator of the ultrasound diagnosis apparatus sets the values of the optimal sample numbers for the image processing process "A" to values that are mutually different in correspondence with the transmission and reception conditions. In the examples shown in FIG. 14A, for "the image processing process: A", the optimal sample number under "transmission and reception condition 1" is set to "a1", whereas the optimal sample number under "transmission and reception condition 2" is set to "a2", and the optimal sample number under "transmission and reception condition 3" is set to "a3". The controlling unit 18 additionally obtains the transmission and reception conditions of the target data so as to obtain an optimal sample number from the table shown FIG. 14A and to determine the parameter "n".

As another example, the size of the image taking target and physical properties of structures may vary among the situations where the organ serving as the image taking target is the heart, where the organ is the liver, and where the organ is a kidney. Accordingly, even if the type of image processing process is the same, the optimal sample numbers used for image processing processes may vary depending on the organ serving as the image taking target. To cope with this situation, as shown in FIG. 14B, the operator or the administrator of the ultrasound diagnosis apparatus sets the values of the optimal sample numbers for the image processing process "A" to values that are mutually different in correspondence with the organs serving as the image taking targets. In the examples shown in FIG. 14B, for "the image processing process: A", the optimal sample number for "organ 1" is set to "a1'", whereas the optimal sample number for "organ 2" is set to "a2'", and the optimal sample number for "organ 3" is set to "a3'". The controlling unit 18 additionally obtains information about the image taking target site of the target data so as to obtain an optimal sample number from the table shown FIG. 14B and to determine the parameter "n".

As yet another example, it is also acceptable to set an optimal sample number for each of sets made up of the three elements such as the type of the image processing process, the ultrasound transmission and reception conditions, and the organ serving as the image taking target. In that situation, as shown in FIG. 14C, the operator or the administrator of the ultrasound diagnosis apparatus sets, for example, the values of the optimal sample numbers used for performing the image processing process "A" on the target data of which the image taking target organ is "organ 1", to values that are mutually different in correspondence with transmission and reception conditions. In the examples shown in FIG. 14C, for "the image processing process: A" and "organ 1", the optimal sample number under "transmission and reception condition 1" is set to "a11", whereas the optimal sample number under "transmission and reception condition 2" is set to "a12", and the optimal sample number under "transmission and reception condition 3" is set to "a13". The controlling unit 18 additionally obtains the transmission and reception conditions and information about the image taking target site of the target data, so as to obtain an optimal sample number from the table shown FIG. 14C and to determine the parameter "n".

In other words, in the second modification example, it is possible to optimize the effect of the image processing process performed on the target data by changing the optimal sample number in consideration of not only the type of the image processing process but also the ultrasound transmission and reception conditions and the information about the organ serving as the image taking target.

In the exemplary embodiments described above, the example is explained in which the data processing unit 163 performs the image processing process on the low-frequency component data satisfying the optimal sample number; however, it is also acceptable to configure the exemplary embodiments in such a manner that the data processing unit 163 performs the image processing process on all or a part of the group of data that has been output by the decomposing unit 162 and satisfies the optimal sample number. In other words, the exemplary embodiments are applicable to the situation where the image processing process is performed on the data (the high-frequency decomposed image data) including the high-frequency components as well as on the low-frequency component data. Alternatively, the exemplary embodiments are also applicable to the situation where the image processing process is performed only on the data (the high-frequency decomposed image data) including the high-frequency components. For example, the data processing unit 163 may perform the intended image processing process "A" on all or a part of "HL, LH, and HH" shown in FIG. 4 as well as on "LL" shown in FIG. 4. In that situation, the reconstructing unit 164 generates reconstructed data by using an already-processed group of data output by the data processing unit 163. Thus, it is possible to optimize the effect of the image processing process by performing the intended image processing process on the high-frequency decomposed image data as well as on the low-frequency component data.

Further, the image processing process performed on the high-frequency decomposed image data may be an image processing process other than the intended image processing process. The high-frequency decomposed image data (e.g., "HL, LH, and HH" shown in FIG. 4) including the high-frequency components contains edge information. Thus, for example, the data processing unit 163 performs an edge detecting process on the high-frequency decomposed image data. Further, for example, the data processing unit 163 judges whether a detected edge represents a contour of a structure or noise. Further, for example, if the edge represents a contour of a structure, the data processing unit 163 performs an edge enhancing process. In contrast, if the edge represents noise, the data processing unit 163 performs a noise eliminating process. The data processing unit 163 performs either the image processing process using the edge detection described above or the intended image processing process and the image processing process using the edge detection described above, on the high-frequency decomposed image data. As a result of the process, the data processing unit 163 is able to further optimize the effect of the intended image processing process. It is also acceptable to configure the data processing unit 163 so as to perform the image processing process using the edge detection described above as well as the intended image processing process, also on the low-frequency component data.

Further, in the exemplary embodiments above, the example is explained in which the ultrasound diagnosis apparatus serving as a medical image diagnosis apparatus performs the image processing process on the target data, while taking the optimal sample number into consideration. However, the processes described in the exemplary embodiments may be performed by another medical image diagnosis apparatus such as an X-ray diagnosis apparatus, an X-ray CT apparatus, an MRI apparatus, a Single Photon Emission Computed Tomography (SPECT) apparatus, or a Positron Emission Computed Tomography (PET) apparatus, while using the data generated by the medical image diagnosis apparatus as a target. In other words, the target data may be data used for generating medical images such as data obtained by detecting radiation or data from magnetic resonance signals or may be various types of medical image data.

Further, the processes explained in the exemplary embodiments may be performed by an image processing apparatus that is provided independently of a medical image diagnosis apparatus. More specifically, an arrangement is acceptable in which an image processing apparatus having the functions of the image processing unit 16 and the controlling unit 18 shown in FIG. 1 receives the target data from a database of a Picture Archiving and Communication System (PACS), which is a system for managing data of various types of medical images, or from a database of an electronic medical record system that manages electronic medical records to which medical images are attached and performs the processes explained in the exemplary embodiments on the received target data.

Further, the processes explained in the exemplary embodiments are also applicable to situations where the target data is three-dimensional. For example, it is possible to apply the processes explained in the exemplary embodiments by treating three-dimensional target data as a plurality of pieces of two-dimensional target data arranged along a predetermined direction.

Furthermore, the process of determining the parameter "n" explained in the exemplary embodiments may be automatically performed by the controlling unit 18 or may be determined by the operator for each image processing process.

As explained above, according to an aspect of the exemplary embodiments, it is possible to optimize the effect of the image processing process.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
an enlarging unit configured to generate enlarged data by enlarging target data serving as a target of an image processing process, while using an enlargement factor based on an optimal sample number indicating a quantity of samples per unit length that is suitable for the image processing process;
a decomposing unit configured to generate a group of data satisfying the optimal sample number by performing a decomposing process on the enlarged data, the decomposing process being realized by a multi-resolution analysis having a predetermined number of stages based on the enlargement factor;

a data processing unit configured to generate an already-processed group of data by performing the image processing process on the group of data satisfying the optimal sample number;

a reconstructing unit configured to generate reconstructed data by performing a reconstructing process realized by a multi-resolution analysis having the predetermined number of stages on the already-processed group of data; and a reducing unit configured to generate reduced data by reducing the reconstructed data in such a manner that a quantity of samples per unit length becomes equal to a quantity of samples per unit length in the target data.

2. The image processing apparatus according to claim 1, wherein the enlarging unit generates the enlarged data while using the enlargement factor that causes the quantity of samples per unit length in the target data to be a power of 2 of the optimal sample number.

3. The image processing apparatus according to claim 1, wherein the target data is data generated based on a reflected wave of an ultrasound wave.

4. The image processing apparatus according to claim 3, wherein the optimal sample number is changed according to one or both of an ultrasound transmission and reception condition and an organ serving as an image taking target, as well as according to a type of the image processing process.

5. The image processing apparatus according to claim 1, wherein, if the target data has been enlarged or reduced from original data, the optimal sample number is changed according to an enlargement factor or a reduction factor applied to the original data to arrive at the target data.

6. The image processing apparatus according to claim 1, wherein, if the quantity of samples per unit length in the target data is equal to or smaller than the optimal sample number:

the enlarging unit generates the enlarged data by enlarging the target data while using the enlargement factor that causes the quantity of samples per unit length in the target data to be equal to the optimal sample number, the data processing unit performs the image processing process on the enlarged data, and the reducing unit generates the reduced data by reducing processing target data resulting from the image processing process performed on the enlarged data, in such a manner that a quantity of samples per unit length in the processing target data becomes equal to the quantity of samples per unit length in the target data.

7. The image processing apparatus according to claim 1, wherein the decomposing unit performs a wavelet transform as the decomposing process realized by the multi-resolution analysis, and the reconstructing unit performs a wavelet inverse transform as the reconstructing process realized by the multi-resolution analysis.

8. A medical image diagnosis apparatus comprising:

an enlarging unit configured to generate enlarged data by enlarging target data serving as a target of an image processing process, while using an enlargement factor based on an optimal sample number indicating a quantity of samples per unit length that is suitable for the image processing process;

a decomposing unit configured to generate a group of data satisfying the optimal sample number by performing a decomposing process on the enlarged data, the decomposing process being realized by a multi-resolution analysis having a predetermined number of stages based on the enlargement factor;

a data processing unit configured to generate an already-processed group of data by performing the image processing process on the group of data satisfying the optimal sample number;

a reconstructing unit configured to generate reconstructed data by performing a reconstructing process realized by a multi-resolution analysis having the predetermined number of stages on the already-processed group of data; and a reducing unit configured to generate reduced data by reducing the reconstructed data in such a manner that a quantity of samples per unit length becomes equal to a quantity of samples per unit length in the target data.

* * * * *